(12) United States Patent
Khanicheh et al.

(10) Patent No.: US 10,674,894 B2
(45) Date of Patent: Jun. 9, 2020

(54) SYSTEMS AND METHODS FOR DEVICE EXCHANGE IN AN ENDOSCOPIC PROCEDURE

(71) Applicant: HOYA Corporation, Tokyo (JP)

(72) Inventors: Azadeh Khanicheh, Somerville, MA (US); Isaac Ostrovsky, Wellesley, MA (US); Michael Barenboym, Boston, MA (US); Almir Velagic, Watertown, MA (US)

(73) Assignee: HOYA CORPORATION, Tokyo (JP)

( * ) Notice: Subject to any disclaimer, the term of this patent is extended or adjusted under 35 U.S.C. 154(b) by 508 days.

(21) Appl. No.: 15/585,487

(22) Filed: May 3, 2017

(65) Prior Publication Data

US 2018/0317745 A1 Nov. 8, 2018

(51) Int. Cl.
*A61B 1/00* (2006.01)
*A61B 1/018* (2006.01)
*A61B 1/01* (2006.01)

(52) U.S. Cl.
CPC ........ *A61B 1/0014* (2013.01); *A61B 1/00064* (2013.01); *A61B 1/00087* (2013.01); *A61B 1/00121* (2013.01); *A61B 1/00128* (2013.01); *A61B 1/01* (2013.01); *A61B 1/018* (2013.01)

(58) Field of Classification Search
None
See application file for complete search history.

(56) References Cited

U.S. PATENT DOCUMENTS

| | | | |
|---|---|---|---|
| 4,988,356 A | * | 1/1991 | Crittenden ........ A61M 25/0169 600/434 |
| 6,893,393 B2 | | 5/2005 | Carrillo |
| 7,172,577 B2 | | 2/2007 | Mangano et al. |

(Continued)

FOREIGN PATENT DOCUMENTS

WO WO 1998/010821 3/1998

OTHER PUBLICATIONS

Boston Scientific Corporation, May 2016, "Dreamtome RX Sphincterotome" Brochure, ENDO-377607-AA (6 pages).

(Continued)

*Primary Examiner* — Timothy J Neal
(74) *Attorney, Agent, or Firm* — Finnegan, Henderson, Farabow, Garrett & Dunner, LLP

(57) ABSTRACT

Embodiments of the present disclosure are directed to systems and methods for device exchange in an endoscopic procedure. In one implementation, a system for device exchange in an endoscopic procedure includes an elongated device having a slit extending from a distal end to a proximal end of the elongated device, a main block, and an adapter. The main block is configured to be affixed to a port of an endoscope. The main block includes a main channel for receiving a guidewire and the elongated device. The adapter can be engaged with the main block and configured to merge the guidewire into the elongated device. The adapter includes a working channel for receiving the elongated device and a working member raising from an inner wall of the working channel. When the elongated device passes through the working channel, the working member wedges open a portion of the slit of the elongated device such that a portion of the guidewire merges into the elongated device through the opened portion of the slit.

25 Claims, 15 Drawing Sheets

(56) References Cited

U.S. PATENT DOCUMENTS

| | | |
|---|---|---|
| 2002/0143251 A1 | 10/2002 | Richardson et al. |
| 2003/0233043 A1 | 12/2003 | Windheuser et al. |
| 2005/0059990 A1 | 3/2005 | Ayala et al. |
| 2009/0221873 A1* | 9/2009 | McGrath ............ A61B 1/00128 600/153 |

OTHER PUBLICATIONS

International Search Report and Written Opinion of the International Searching Authority for International Application No. PCT/IB2018/000583 dated Sep. 24, 2018.

* cited by examiner

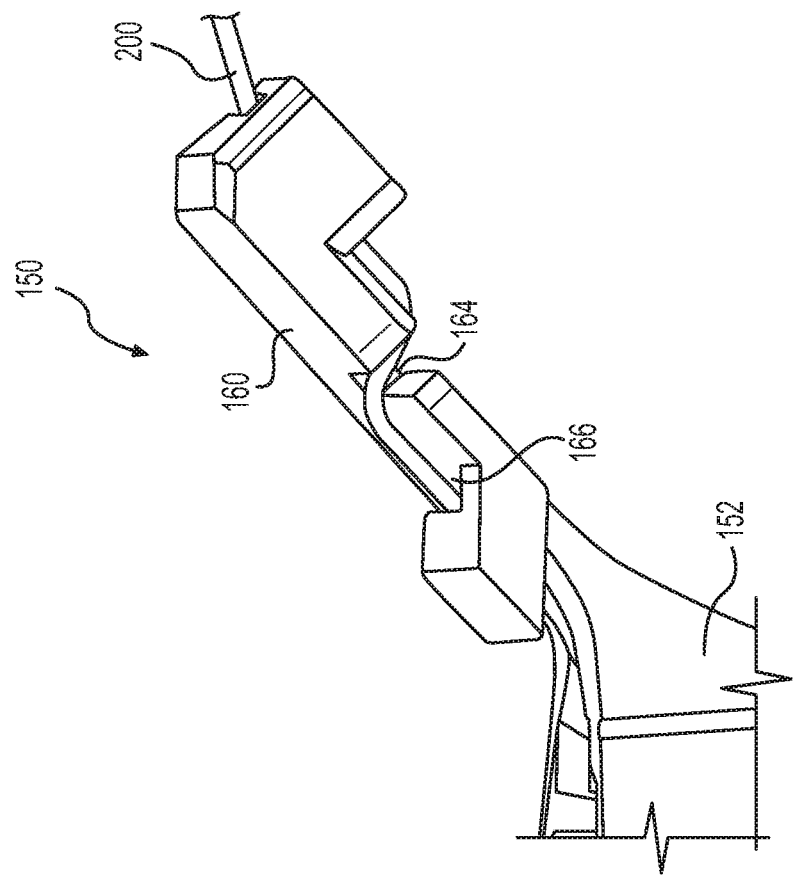
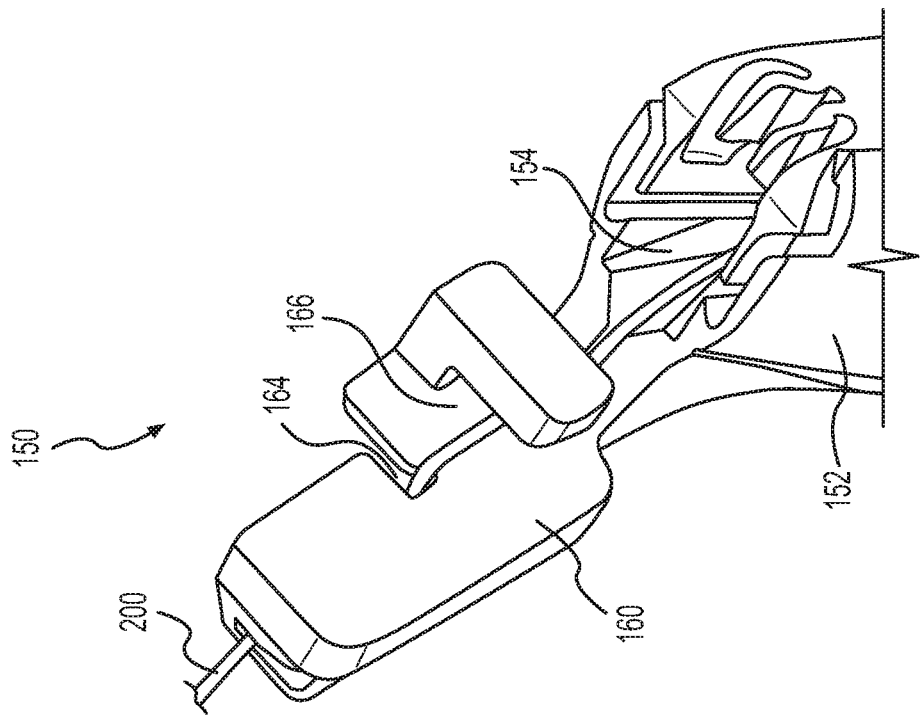
FIG. 6
FIG. 5

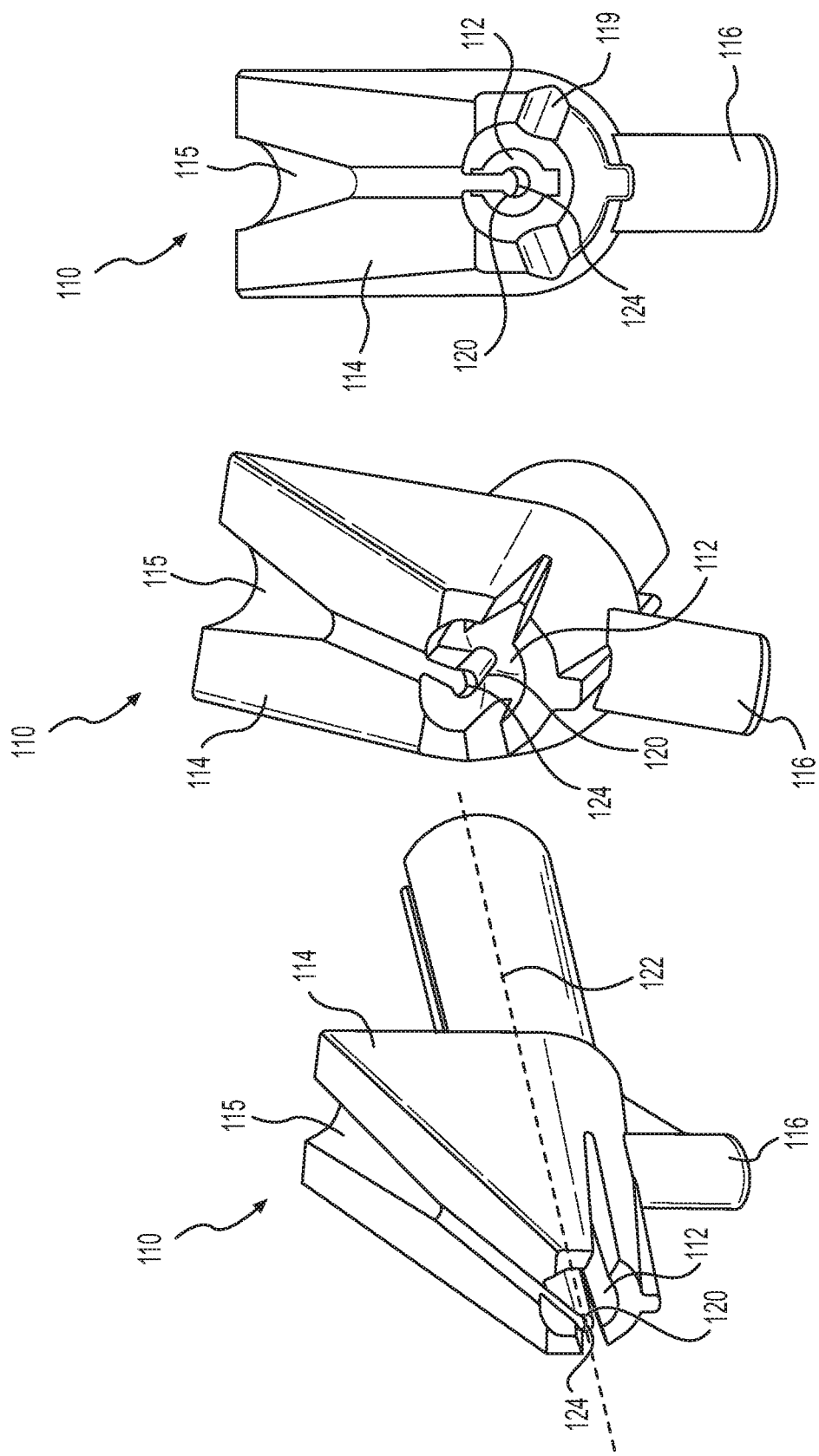

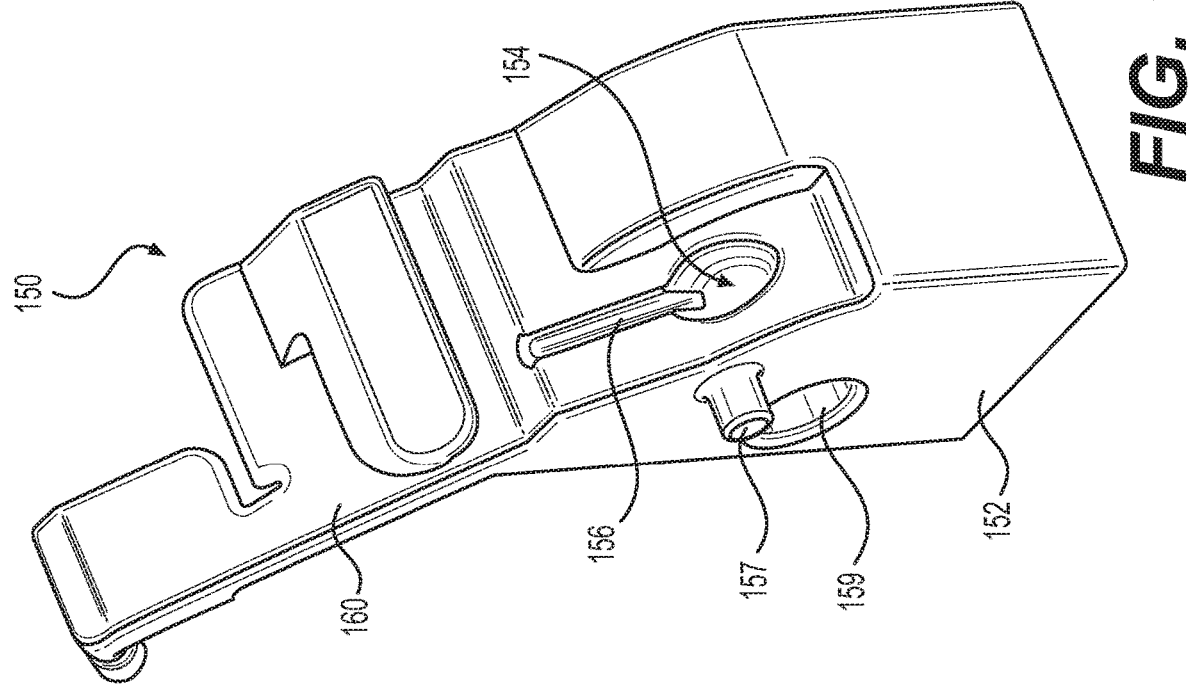

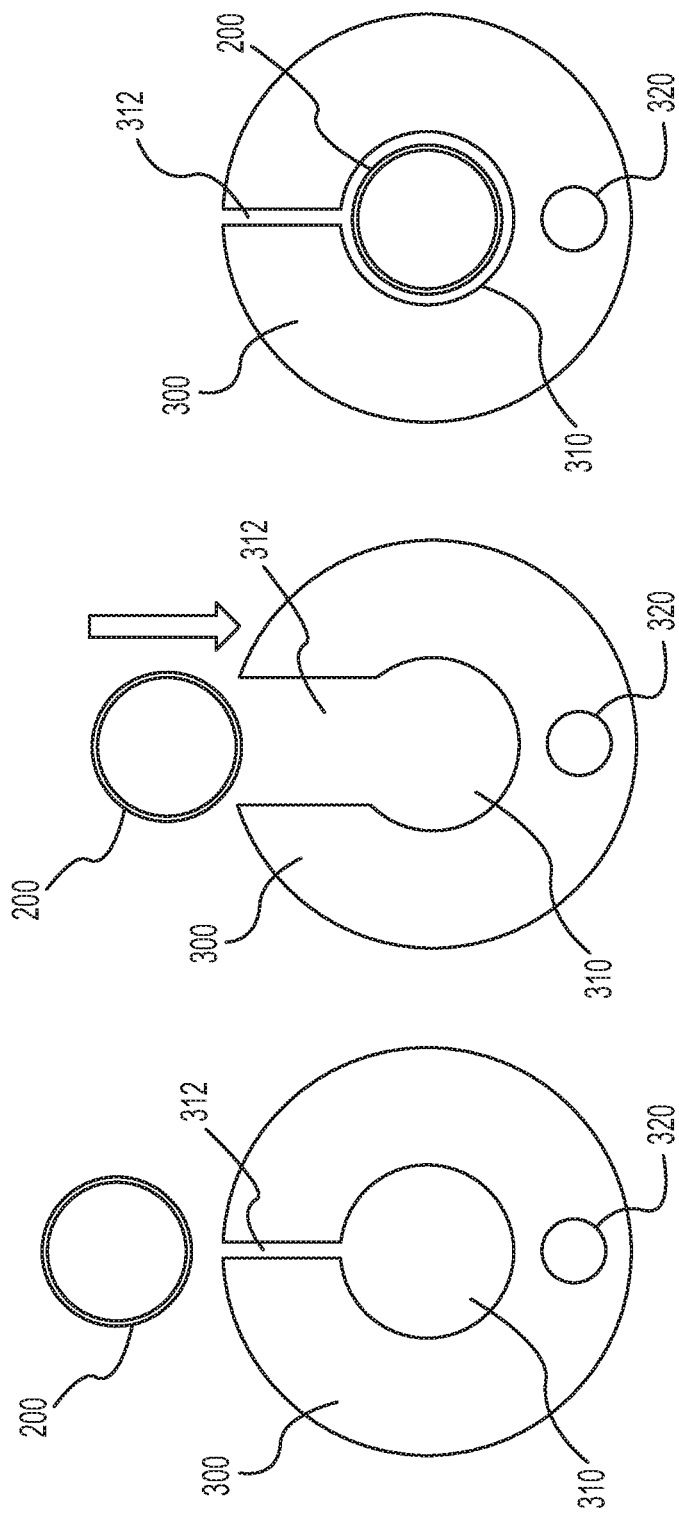

SYSTEMS AND METHODS FOR DEVICE EXCHANGE IN AN ENDOSCOPIC PROCEDURE

BACKGROUND

Technical Field

The present disclosure generally relates to endoscopic systems and methods of use. More particularly, and without limitation, the disclosed embodiments relate to apparatuses, systems, and methods for exchanging elongated devices in an endoscopic procedure.

Background Description

Endoscopic procedures often require the introduction of multiple devices in parallel or in series through the internal working lumen of an endoscope. For example, in an endoscopic retrograde cholangiopancreatography (ERCP) procedure, multiple devices need to be introduced into the lumen of a duodenosope to diagnose and treat certain problems of the biliary or pancreatic ductal systems. Typically, an initial operation is performed to introduce a first device through the ampullary orifice (papilla of Vater), and then into the biliary tree until the distal end of the first device is proximate to a desired site in the biliary tree. The first device may be a cannula (catheter) or a sphincterotome. The initial operation can be diagnostic, such as injecting contrast agents through the device to visualize the biliary tree, or therapeutic, such as enlarging the ampullary orifice.

In many instances, initial visualization could reveal one or more sites in the biliary tree that require further therapeutic operations, such as to remove a stone, open a stricture, or sample tissue at these sites. In such instances, additional devices, such as a balloon, a basket, or a stent delivery catheter, may need to be subsequently introduced into the lumen of the duodenoscope to a desired treatment site. Thus, to facilitate introducing these additional devices to the desired treatment site, a guidewire introduced with the first device is typically held in place in the endoscope to maintain access to the desired treatment site. Removing the first device and introducing the additional devices over the guidewire would allow for continued access to the desired treatment site of the additional devices. However, displacement of the guidewire during this exchange process can result in loss of access to the desired treatment site, which then requires a difficult, time-consuming, and tedious operation to re-direct the guidewire to the desired treatment site.

Two techniques are generally used for device exchange. One is termed the "long wire" or "over the wire" technique, and the other is termed the "short wire" technique. The long wire technique uses an extra-long guidewire, whose length is typically longer than the lumen of the endoscope plus the length of the device introduced over the guidewire. In other words, the length of the guidewire extending out of the endoscope needs to be at least as long as that of the device to be replaced. This allows a proximal end of the guidewire to be securely controlled at all times by the physician or an assistant to maintain the position of the guidewire and thus the access to the desired treatment site. To remove the first device off the guidewire, the physician and the assistant must make a series of precise and coordinated maneuvers until the first device is completely off the guidewire. Then, a second device can be introduced over the guidewire through a similarly tedious coordination between the physician and assistant. Throughout this exchange process, the physician lacks or has a limited control of the guidewire, which could result in movement or displacement of the distal end of the guidewire and thus loss of access to the desired treatment site.

To address the shortcomings of the long wire technique, the short wire technique allows the physician to maintain control of the guidewire most of the time during the exchange. In the short wire technique, the guidewire is enclosed in the first device for a short distance from the distal end to a proximal point of the first device. While the guidewire is held in place, typically by a locking device installed on the biopsy port of the endoscope, a physician can remove the first device by splitting or tearing away the device from the guidewire up to the proximal point of the first device. Then, the physician can perform a short wire exchange that does not require the series of precise coordination between the physician and the assistant as in the long wire exchange. The second device can be introduced by feeding its distal end over the proximal end of the guidewire for the short distance. However, during this short wire exchange, the guidewire is unlocked from the locking device and re-locked after the second device is introduced over the guidewire for the short distance. The locking and unlocking of the guidewire during the short wire exchange still require the physician or the assistant to manually hold the guidewire in place during the device exchange. This is time-consuming and could result in movement or displacement of the distal end of the guidewire and thus loss of access to the desired treatment site.

Therefore, an improved system or apparatus is needed that allows the guidewire to remain locked in a desired position to maintain access to the desirable treatment site during the device exchange in an endoscopic procedure. Such apparatus or system may be capable of reducing the time taken for a physician to perform an endoscopic procedure and increasing the effectiveness of the procedure.

SUMMARY

The embodiments of the present disclosure include apparatuses, systems, and methods for exchanging elongated devices in an endoscopic procedure. Advantageously, the exemplary embodiments allows for locking a guidewire in a desired position to maintain access to a desirable treatment site during the exchange, thereby improving the efficiency and effectiveness of the endoscopic procedure.

According to an exemplary embodiment of the present disclosure, a system for device exchange in an endoscopic procedure is described. The system includes an elongated device, a main block, and an adapter. The elongated device has a slit extending over its length. The main block is configured to be affixed to a port of an endoscope. The main block includes a main channel for receiving a guidewire and the elongated device. The adapter can be fixedly or removably engaged with the main block and configured to merge the guidewire into the elongated device. The adapter includes a working channel for receiving the elongated device and a working member raising from an inner wall of the working channel. When the elongated device passes through the working channel, the working member wedges open a portion of the slit of the elongated device such that a portion of the guidewire merges into the elongated device through the opened portion of the slit.

According to a further exemplary embodiment of the present disclosure, an apparatus for device exchange in an endoscopic procedure is described. The apparatus includes a main block configured to be affixed to a port of an endoscope and an adapter configured to be fixedly or removably engaged with the main block. The main block includes a main channel for receiving a guidewire and an elongated device having a slit extending over its length. The adapter is configured to merge the guidewire into the elongated device. The adapter includes a working channel for receiving the elongated device and a working member raising from an inner wall of the working channel. When the elongated device passes through the working channel, the working member wedges open a portion of the slit of the elongated device such that a portion of the guidewire merges into the elongated device through the opened portion of the slit.

According to a yet further exemplary embodiment of the present disclosure, a method for device exchange in an endoscopic procedure is described. The method includes providing an elongated device having a slit extending over its length and an apparatus for device exchange. The apparatus includes a main block configured to be affixed to a port of an endoscope and an adapter configured to be fixedly or removably engaged with the main block. The main block includes a main channel for receiving a guidewire and the elongated device. The adapter includes a working channel for receiving the elongated device and a working member raising from an inner wall of the working channel. The method further includes receiving the elongated device through the working channel of the adapter such that the elongated device passes by the working member. The method also includes wedging open a portion of a slit of the elongated device by the working member and merging a portion of the guidewire into the elongated device through the opened portion of the slit.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 5 is a partial perspective view of an exemplary locking device of the exemplary system of FIG. 1, according to embodiments of the present disclosure.

FIG. 6 is another partial perspective view of the exemplary locking device of FIG. 5, according to embodiments of the present disclosure.

FIG. 9 is a perspective view of the exemplary adapter of FIG. 8, according to embodiments of the present disclosure.

FIG. 10 is another perspective view of the exemplary adapter of FIG. 8, according to embodiments of the present disclosure.

FIG. 11 is bottom plan view of the exemplary adapter of FIG. 8, according to embodiments of the present disclosure.

FIG. 15 is a partial perspective view of another exemplary main block of the exemplary system of FIG. 1, according to embodiments of the present disclosure.

FIG. 20A is a parallel cross-sectional view of the exemplary guidewire of FIG. 7 before merging into the exemplary elongated device of FIG. 7, according to embodiments of the present disclosure.

FIG. 20B is a parallel cross-sectional view of the exemplary guidewire of FIG. 7 merging into the exemplary elongated device of FIG. 7, according to embodiments of the present disclosure.

FIG. 20C is a parallel cross-sectional view of the exemplary guidewire of FIG. 7 merged into the exemplary elongated device of FIG. 7, according to embodiments of the present disclosure.

DETAILED DESCRIPTION

Figure 1:
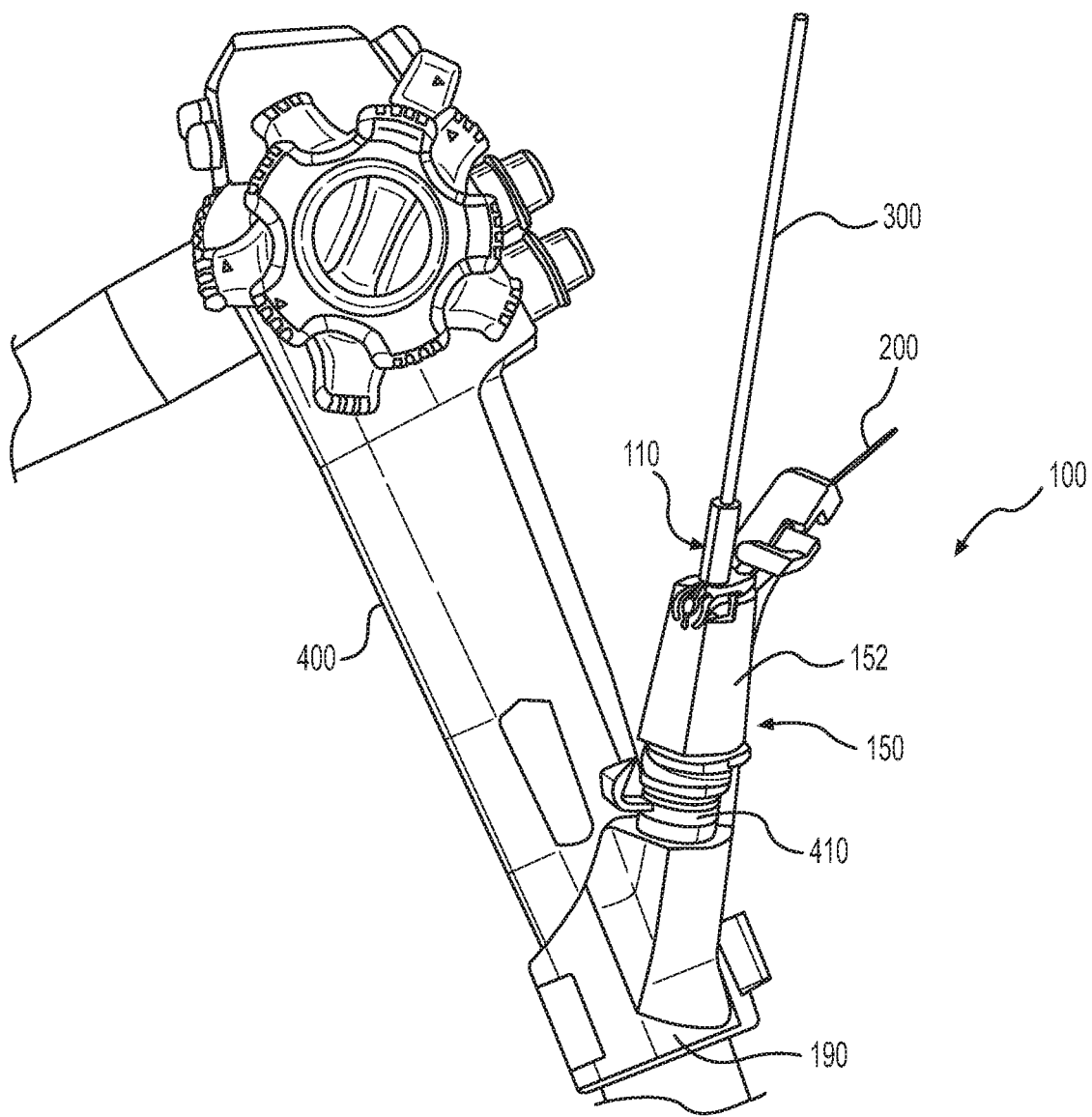
FIG. 1 is a perspective view of an exemplary system for device exchange, according to embodiments of the present disclosure.

The disclosed embodiments relate to systems, apparatuses, and methods for efficient and effective device exchange in an endoscopic procedure. Embodiments of the present disclosure can be implemented in an endoscopic system for performing suitable diagnostic and/or therapeutic operations to one or more desired treatment sites in the cardiovascular system, the gastrointestinal system, or the respiratory system. Advantageously, embodiments of the present disclosure allow for fixing at least one guidewire to a desired position during the exchange of devices through the lumen of an endoscope, thereby maintaining access to at least one desired treatment site.

As described herein, an endoscope typically includes a proximal end and a distal end, and has an internal lumen extending between the distal end and the proximal end. A proximal end may refer to a point or a location along the length of the endoscope closer to a physician or a medical practitioner. A distal end may refer to a point or location along the length of the endoscope closer to a treatment site in the body of a patient during an endoscopic procedure. A device is typically introduced into the lumen of the endoscope from the proximal end to the distal end of the endoscope until a distal end of the device approximates or reaches a desired treatment site.

According to an aspect of the present disclosure, a system for device exchange in an endoscopic procedure may include one or more elongated devices (for example, cannula, sphincterotome, balloon, basket, brushes, forceps, etc.) to be exchanged. The elongated devices may each have a slit extending over at least a substantial length of the device, for example, extending from a distal end to a proximal end of the device. Unlike devices used in the short wire exchange technique, the slit allows the elongated device to be removed off a guidewire by being split or separated from the guidewire via the slit at the proximal end of the endoscope continuously up to the distal end of the elongated device. The slit also allows the elongated device to be introduced over the guidewire by merging with the guidewire via the slit continuously until the distal end of the elongated device reaches the desired treatment site. Advantageously, during the device exchange, the guidewire can remain locked in a desired position by a locking device, thereby eliminating the need to manually holding the guidewire by a physician and effectively maintaining a previously obtained access to the desired treatment site.

In some embodiments, a natural width of the slit may be substantially smaller than the diameter of the guidewire. To introduce an elongated device over the guidewire, a portion of the slit is opened or widened, allowing for a portion of the guidewire to merge into a portion of an elongated device. The opened portion of the slit then returns to its natural width after the merge. In some instances, after merging into the elongated device, the guidewire is received by a partially enclosed channel across the longitudinal axis of the elongated device. Advantageously, the transient opening and closing (or widening and narrowing) of the slit allows the introduction of the elongated device over the guidewire as well as retaining the guidewire within the elongated device during a medical operation after the device exchange.

As described herein, the longitudinal axis of the elongated device may refer to a central axis of the elongated device or of an internal channel of the elongated device. Alternatively, the longitudinal axis of the elongated device may refer to an off-center axis of the elongated device or of an internal channel of the elongated device.

According to an aspect of the present disclosure, a system for device exchange in an endoscopic procedure may include an adapter that allows for the introduction of the elongated device over a guidewire. The adapter may include a working channel for receiving the elongated device and a working member raising from an inner wall of the working channel. As the elongated device passes through the working channel, the working member may wedge open a portion of the slit of the elongated device, allowing a portion of the guidewire to merge into a corresponding portion of the elongated device through the opened portion of the slit. After passing by the working member, the opened portion of the slit may return to the natural width, allowing the merged portion of the guidewire to be retained in the elongated device.

The adapter can merge the guidewire into the elongated device as the elongated device passes through the working channel continuously from a distal end of the elongated device until the distal end reaches a desired treatment site. Advantageously, during this continuous merging of the guidewire into the elongated device, rather than being unlocked and manually held in place, the guidewire can remain locked in a desired position, thereby reducing the risk of displacement of the guidewire and thus the risk of losing access to the desired treatment site.

According to an aspect of the present disclosure, a system for device exchange in an endoscopic procedure may include a main block to be affixed to a port of an endoscope. The main block may include a main channel configured to receive at least one guidewire. The main block may fixedly or removably engage with the adapter to introduce an elongated device over a guidewire received in the main channel. When the adapter is engaged with the main block, the longitudinal axis of the working channel of the adapter may align with the longitudinal axis of the main channel. The main block may further include a main groove that may lead the guidewire to be aligned with the longitudinal axis of the main channel, and thus the longitudinal axis of the working channel of the adapter. In such instances, an elongated device passing through the working channel of the adapter would align with the guidewire in the main channel of the main block, which facilitates the merging of the guidewire into the elongated device. Advantageously, the use of the main block and the adapter for introducing an elongated device over a guidewire eliminates the need to perform a long wire or short wire exchange, thereby improving the efficiency and accuracy of device exchange during an endoscopic procedure.

As described herein, the longitudinal axis of the main channel of the main block may refer to a central axis or an off-center axis of the main channel. The longitudinal axis of the working channel of the adapter may refer to a central axis or an off-center axis of the working channel. The longitudinal axis of the elongated device may refer to a central axis or an off-center axis of the elongated device or an inner channel of the elongated device.

In some embodiments, the main block may further include a locking device for fixing the guidewire in a desired position. The desired position may be predetermined after an initial operation before performing the device exchange. The locking device may include zigzag locking features that retain the guidewire in the predetermined desired position by frictionally holding the guidewire in place. The zigzag locking features may be used in combination with other mechanical features that can bend, twist, pinch, clamp, or lock the guidewire in place. In some embodiments, the main groove of the main block may incline from the bottom of the locking device to the longitudinal axis of the main channel such that the guidewire is led towards the longitudinal axis of the main channel, prepared to be merged into an elongated device.

In some embodiments, the main block may include more than one locking devices for locking one or more additional guidewires. The locking devices may use the same or different locking features and/or mechanisms. The main channel may further include secondary grooves for retaining and holding the additional guidewires in place. Each guidewire may be locked or unlocked from the locking features of the locking devices independently, and may be merged into a different elongated device. The ability to receive and lock more than one guidewires advantageously provides the physician more flexibility in selecting and using a suitable number and types of devices for conducting medical operations during an endoscopic procedure.

Reference will now be made in detail to embodiments and aspects of the present disclosure, examples of which are illustrated in the accompanying drawings. Where possible, the same reference numbers will be used throughout the drawings to refer to the same or like parts.

FIG. 1 is a perspective view of an exemplary system 100 for device exchange. As shown in FIG. 1, system 100 may be used in combination with an exemplary endoscope 400 (partially shown) during an endoscopic procedure. System 100 includes an adapter 110, a main block 150, and at least one elongated device 300. Adapter 110 is fixedly or removably engaged with main block 150 and is configured to receive an elongated device 300 to be introduced over a guidewire 200. Main Block 150 includes a main body portion 152 and a fastener 190 that affixes main block 150 to an exemplary port 410 of endoscope 400. Port 410 may be a biopsy port of endoscope 400 that provides access to an inner lumen of endoscope 400. Port 410 may be normally closed by a biopsy valve before use.

Figure 2:
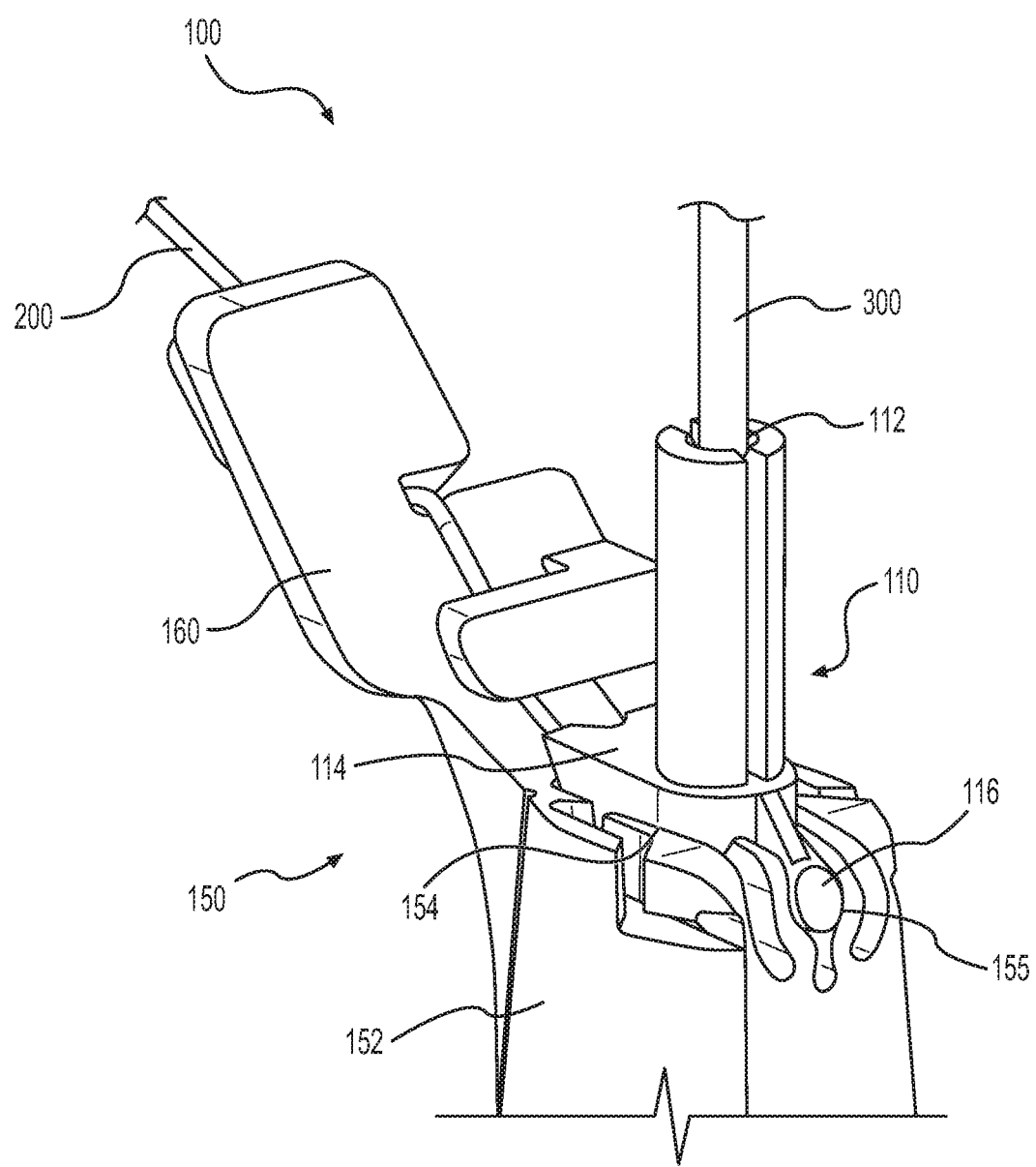
FIG. 2 is a partial perspective view of the exemplary system of FIG. 1, according to embodiments of the present disclosure.
Figure 3:
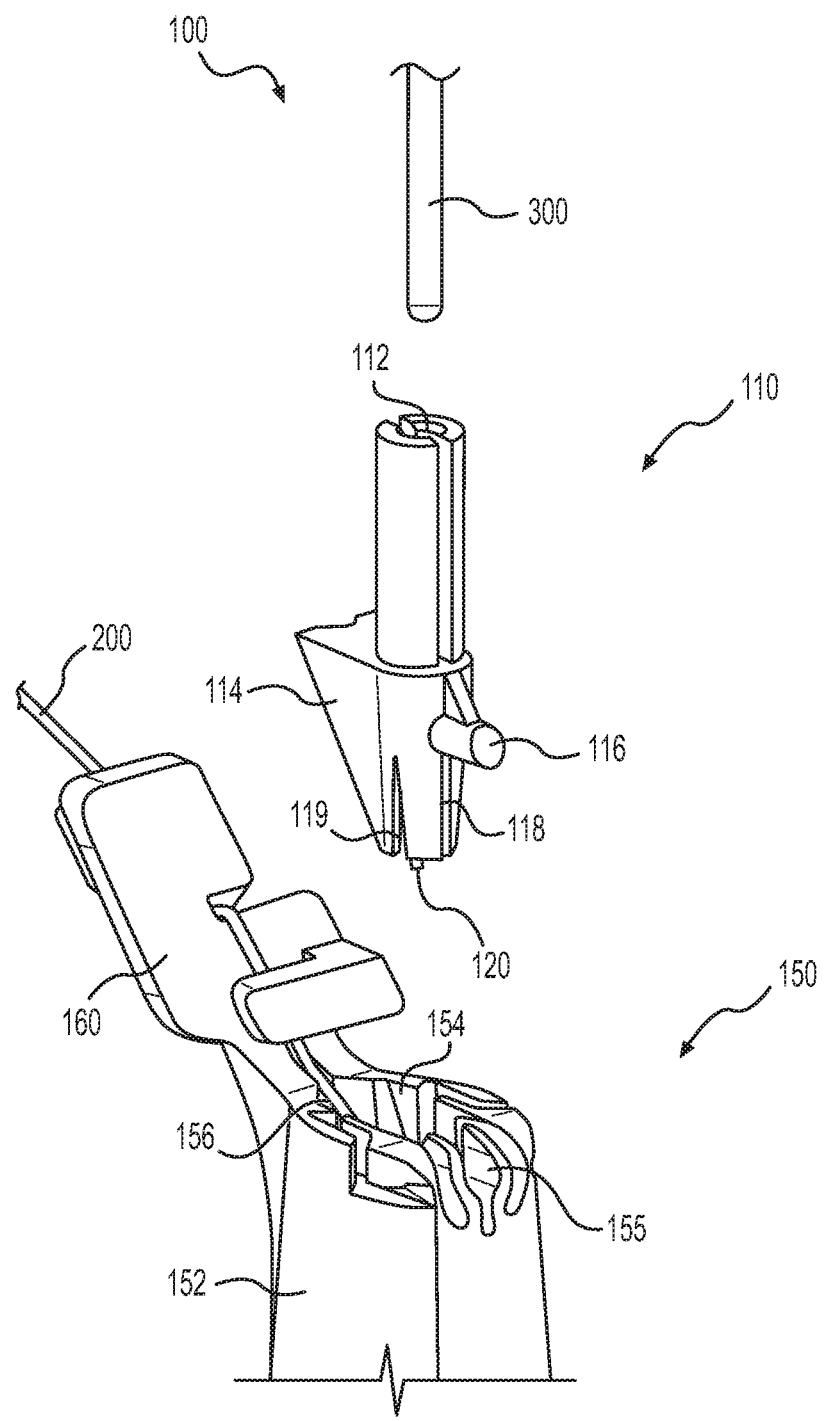
FIG. 3 is a component view of the exemplary system of FIG. 1, according to embodiments of the present disclosure.

FIG. 2 is a partial perspective view of system 100 and FIG. 3 is a component view of system 100. As shown in FIGS. 2 and 3, adapter 110 includes a working channel 112 and a working member 120. Working member 120 may align with a longitudinal axis of working channel 112 such that when elongated device 300 passes though working channel 112, a slit extending along elongated device 300 would pass by working member 120. Working member 120 may open or widen the slit of elongated device 300 as it passes by, as described further below in reference to FIGS. 19A-20C.

Adapter 110 and main block 150 may include one or more complementary fitting structures that allow adapter 110 to fixedly or removably engage with main block 150. For example, adaptor 110 may removably engage with main block via frictional fit, threaded fit, snap fit, etc. In some embodiments, as shown in FIGS. 2 and 3, adapter 110 includes a body 114 that can be fitted within an opening of a main channel 154 of main block 150. For example, body 114 may be jammed in the opening of main channel 154, thereby securing adapter 110 on main block 150.

Adapter 110 and main block 150 may further include other complementary fitting structures. In some embodiments, as shown in FIGS. 2 and 3, adapter 110 includes a protrusion 116 that can engage with a clamp 155 of main block 150. Alternatively or additionally, adapter 110 may further include one or more bars 118 and/or grooves 119 that can engage with complementary channels or protrusions (not shown) in the interior surface of main channel 154. Other suitable mechanical structures may be used alone or in combination with the above-described fitting structures to engage adapter 110 with main block 150. For example, a detent structure or a fastener may be used to engage adapter 110 with main block 150. Accordingly, adaptor 110 may be securely held in main block 150 during the introduction of elongated device 300 over guidewire 200.

Figure 4:
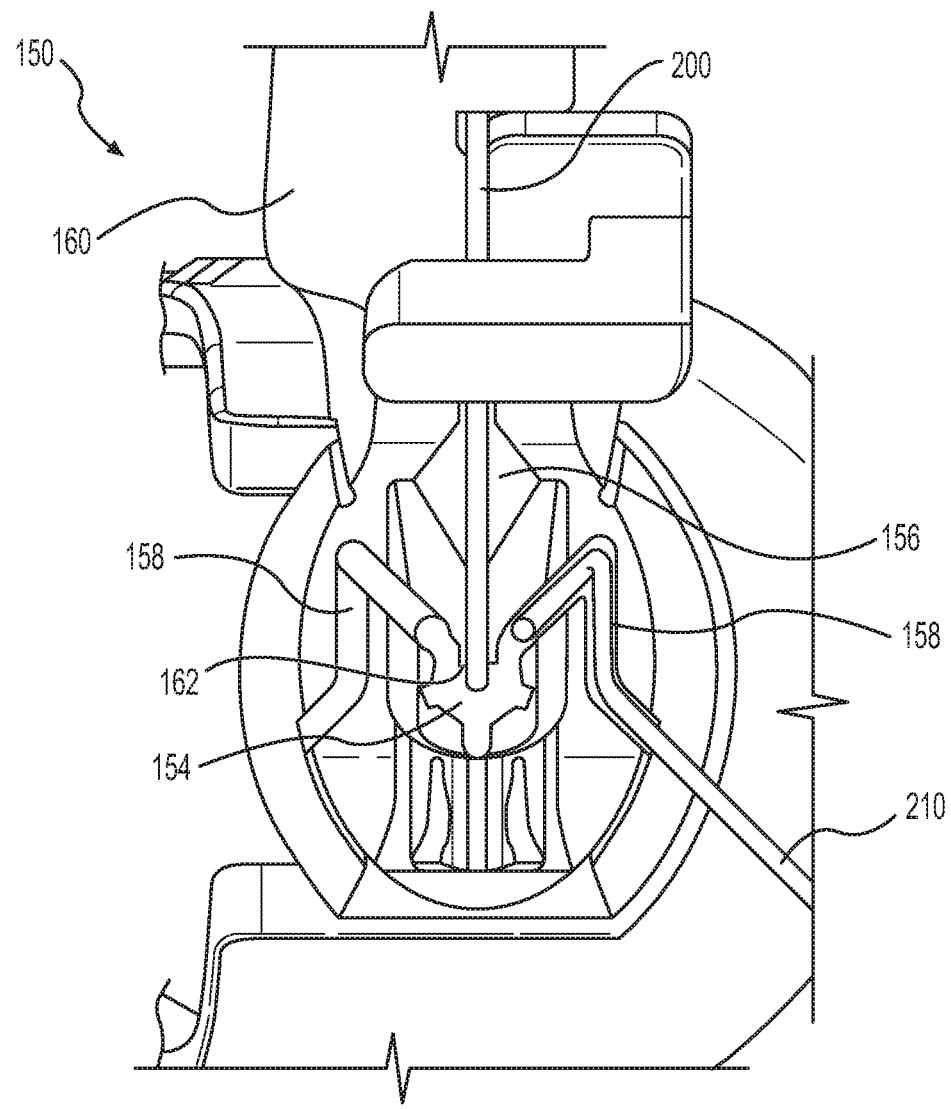
FIG. 4 is partial top plan view of an exemplary main block of the exemplary system of FIG. 1, according to embodiments of the present disclosure.

FIG. 4 is partial top plan view of main block 150. As shown in FIGS. 3 and 4, main block 150 further includes a groove 156 that provides a path for guidewire 200 and a locking device 160 for fixing guidewire 200 in a desired position. Groove 156 may incline from locking device 160 towards the longitudinal axis of main channel 154 such that guidewire 200 is led to be aligned with the longitudinal axis of main channel 154 at a distal end 162 of groove 156. This alignment allows elongated device 300 to be introduced over guidewire 200 as it passes through working channel 112 of adapter 110 as further described below in reference to FIGS. 19A-20C.

More than one guidewires may be received and held in main channel 154. In some embodiments, main channel 154 includes at least one secondary groove for fixing at least one secondary guidewire 210 in a desired position. Guidewire 200 and secondary guidewire 210 may be held to maintain access to the same treatment site or to different treatment sites, for example. In such instances, main block 150 may include at least one additional locking device 160 for locking guidewire 210 in place. Alternatively, as shown in FIG. 4, a secondary locking device 158 may be used for fixing guidewire 210 in place, for example, by pinching, grapping, clamping, or locking guidewires 210. In some embodiments, different elongated devices 300 can be introduced over guidewire 200 and secondary guidewire 210 to perform different operations to the same treatment site or to perform different operations to different treatment sites. In other embodiments, same elongated devices 300 can be introduced over guidewire 200 and secondary guidewire 210 to perform the same operations to different treatment sites.

For example, after a first elongated device 300 is introduced over guidewire 200, guidewire 200 may be moved from main groove 156 to a secondary groove and locked by a secondary locking device 158. The movement may be performed in a controlled fashion such that the access to a treatment site maintained by the distal end of guidewire 200 is maintained. Then, guidewire 210 may be moved into main groove 156 and locked by locking device 160 so that a second elongated device 300 may be introduced over guidewire 210. After the introduction of the second elongated device 300, guidewire 210 may be moved back to a secondary groove and locked by a secondary lock device 158. The use of multiple guidewires and the capability to introduce different devices over multiple guidewires advantageously provide a physician more flexibility in performing desired operations to one or more treatment sites during an endoscopic procedure.

FIGS. 5 and 6 are two different partial perspective views of locking device 160 of main block 150. As shown in FIGS. 5 and 6, locking device 160 may include zigzag locking features that fix guidewire 200 in a desired position by frictionally maintaining guidewire 200 in place. For example, the zigzag locking features of locking device 160 may include a plurality of gaps 164 and slots 166. The size of gaps 164 and slots 166 may be approximately the same or smaller than the diameter of guidewire 200 such that guidewire 200 is frictionally held in place by passing through gaps 164 and slots 166. In some embodiments, the zigzag locking features of locking device 160 may be used in combination with other mechanical features that can bend, twist, pinch, clamp, or lock guidewire 200 in place. As shown in FIGS. 4 and 5, guidewire 200 locked by locking device 160 may extend over main groove 156, which leads guidewire 200 towards the longitudinal axis of main channel 154, prepared to be merged with elongated device 300.

Figure 7:
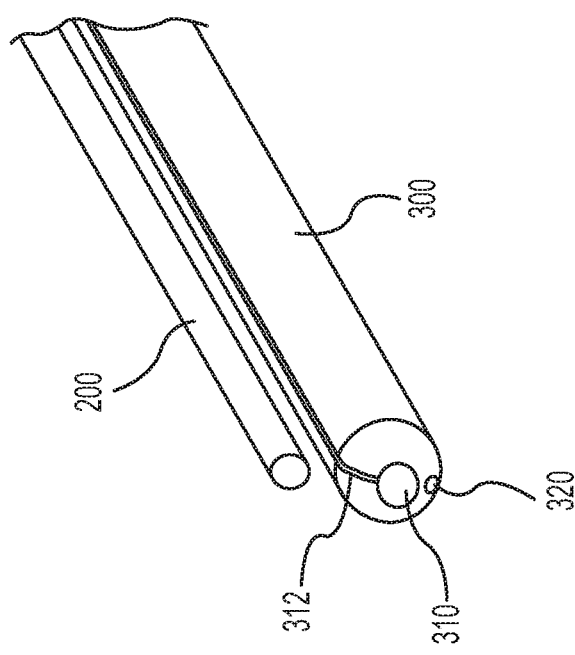
FIG. 7 is a perspective view of an exemplary guidewire and an exemplary elongated device, according to embodiments of the present disclosure.

FIG. 7 is a perspective view of guidewire 200 juxtaposed with elongated device 300. As shown in FIG. 7, elongated device 300 includes a slit 312 and a partially enclosed channel 310 connected to slit 312. Channel 310 and/or slit 312 may extend from a distal end of elongated device 300 to a proximal end of elongated device 300. As described herein, the distal end of elongated device 300 may refer to the distal tip of elongated device 300. The proximal end of elongated device may refer to the proximal tip of elongated device 300 or a location close to the proximal tip of elongated device 300. In some embodiments, as shown in FIG. 7, channel 310 and/or slit 312 extend over the length or a substantial length of elongated device 300 along its longitudinal axis.

Guidewire 200 may be merged into channel 310 through slit 312. In addition, slit 312 allows elongated device 300 to be removed off guidewire 200 merged into channel 310 by being split or separated from guidewire 200 via slit 312. In some embodiments, elongated device 300 may include at least one inner lumen 320 for receiving a secondary device (not shown) or injecting fluids such as contrast to perform a medical operation. The secondary device may be introduced into elongated device 300 before or after it is merged with guidewire 200.

In some embodiments, as shown in FIG. 7, the diameter of guidewire 200 is substantially greater than a natural width of slit 312. This allows guidewire 200 to be retained within channel 310 of elongated device 300 after merging into channel 310 to effectively guide elongated device 300 to desired treatment sites. However, to merge guidewire 200 into channel 310 of elongated device 300 through slit 312, the width of slit 312 needs to be temporarily enlarged for guidewire 200 to enter as described further below.

As described herein, elongated device 300 may be any device that is normally introduced over a guidewire for performing a medical operation, such as to remove a stone, open a stricture, or sample tissue. For example, elongated device 300 may be a device selected from the group including cannula, sphincterotome, balloon, basket, forceps, snare, biopsy brush, dilator, stent delivery catheter, brachytherapy catheter, and lithotripter.

Figure 8:
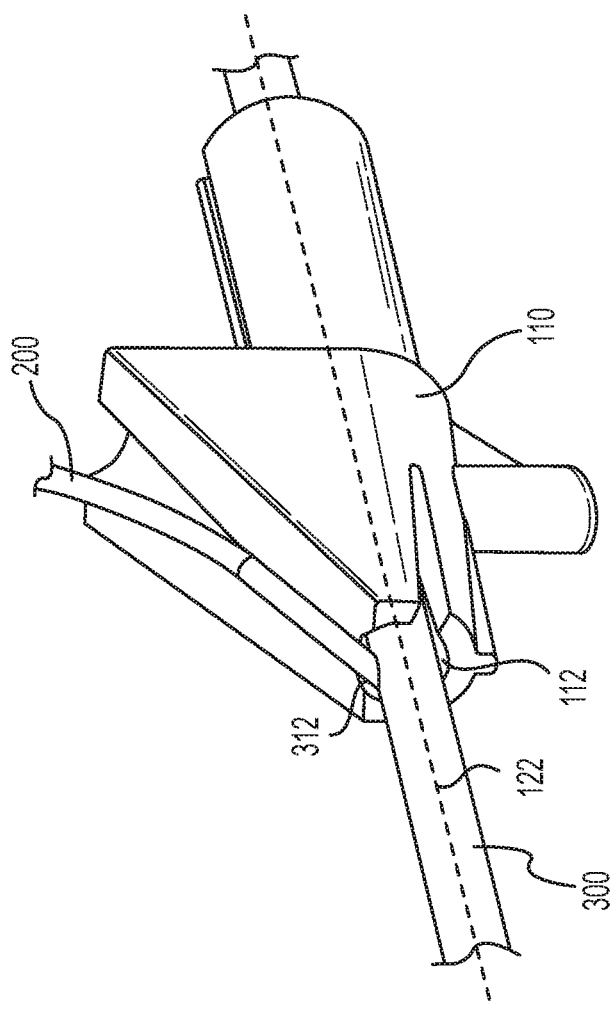
FIG. 8 is a perspective view of an exemplary adapter of the exemplary system of FIG. 1 for merging the exemplary guidewire of FIG. 7 into the exemplary elongated device of FIG. 7, according to embodiments of the present disclosure.

FIG. 8 illustrates the use of adapter 110 for merging guidewire 200 into elongated device 300 through slit 312. As shown in FIG. 8, elongated device 300 is passed through working channel 112 of adapter 110 along a longitudinal axis 122 of working channel 112. Guidewire 200 is merged into slit 312 of elongated device 300 when elongated device 300 passes by working member 120 (not shown), which opens or widens slit 312 to receive the nearby portion of guidewire 200 there through. Features of adapter 100 that allow for merging of guidewire into elongated device 300 are described below in reference to FIGS. 9-14. The working mechanism of adapter 110 is described in detail below in reference to FIGS. 19A-20C.

As described herein, adapter 110 may have any suitable geometry and/or mechanical features to be securely fit into main block 150 and/or to merge guidewire 200 into elongated device 300. Exemplary embodiments and/or features of adaptor 110 are described below with reference to FIGS. 9-14.

Figure 14:
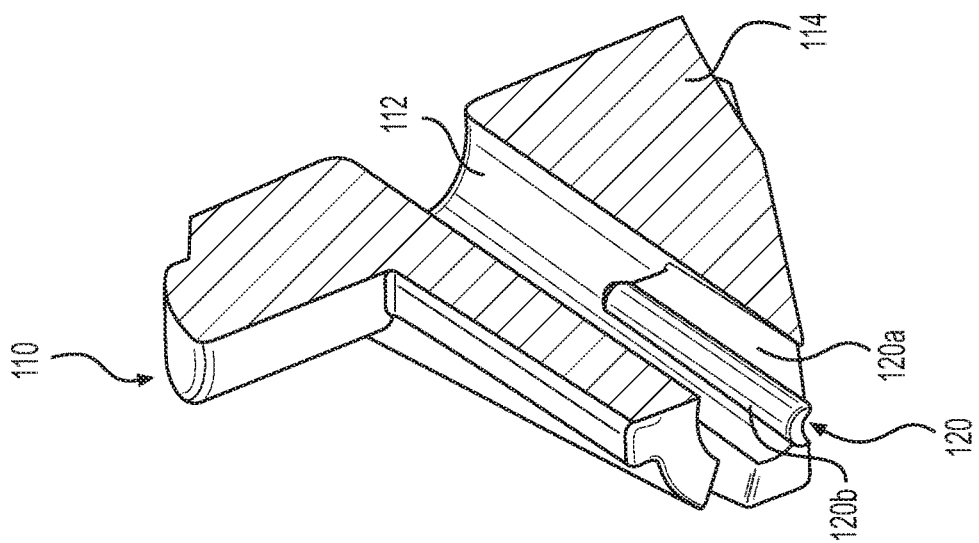
FIG. 14 is another cross-sectional view of the exemplary adapter of FIG. 12, according to embodiments of the present disclosure.
Figure 13:
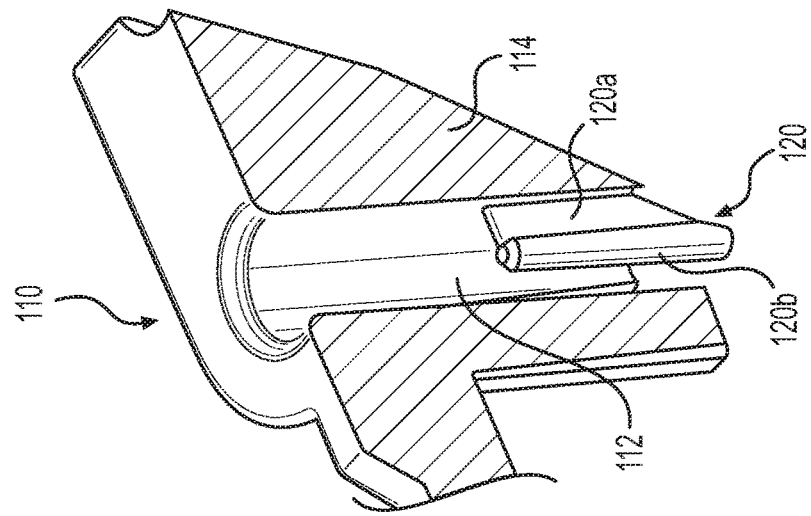
FIG. 13 is a cross-sectional view of the exemplary adapter of FIG. 12, according to embodiments of the present disclosure.
Figure 12:
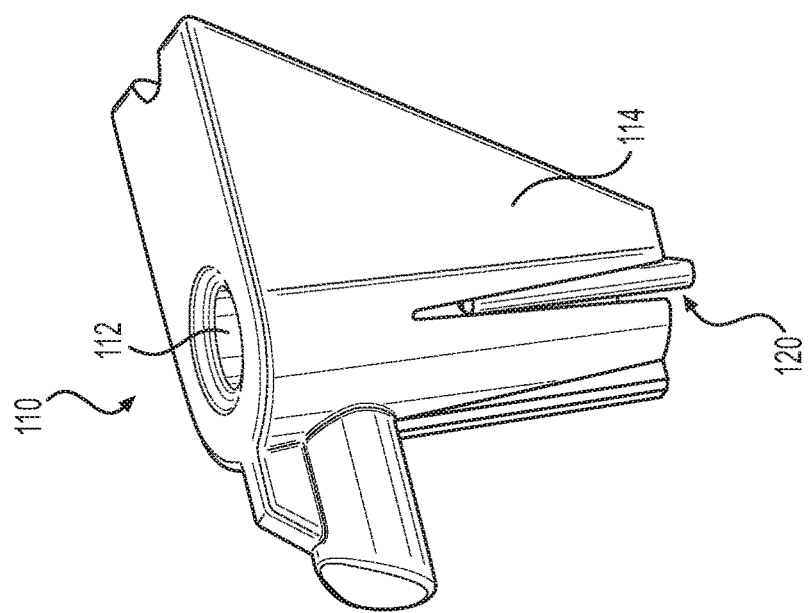
FIG. 12 is a perspective view of another exemplary adapter, according to embodiments of the present disclosure.

FIGS. 9 and 10 are different perspective views of an exemplary embodiment of adapter 110. FIG. 11 is a bottom plan view of the exemplary embodiment of adapter 110 of FIGS. 9 and 10. FIG. 12 is a perspective view of another exemplary embodiment of adapter 110. FIGS. 13 and 14 are cross-sectional views of the exemplary embodiment of adapter 110 of FIGS. 13 and 14.

Figure 18:
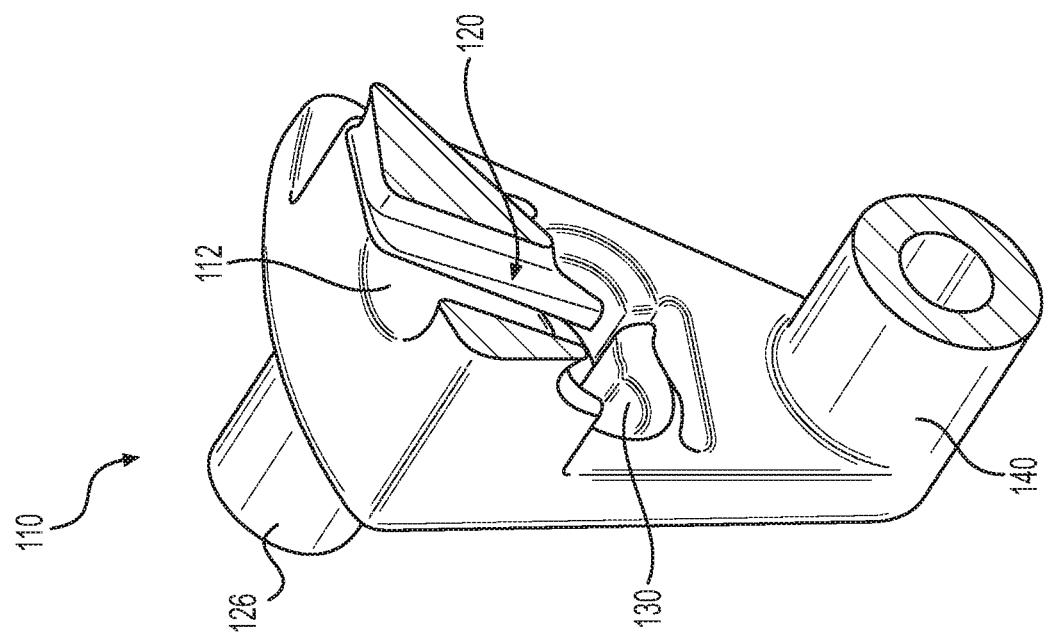
FIG. 18 is a cross-sectional view of the exemplary adaptor of FIG. 16, according to embodiments of the present disclosure.

As described above and shown in FIGS. 9-14, adapter 110 includes working channel 112, working member 120, and body 114. Working member 120 of adapter 110, as shown in FIGS. 9-14, extends from an inner surface of working channel 112 to longitudinal axis 122 of working channel 112. In one exemplary embodiment, working channel 112 extends beyond body 114, as shown in FIGS. 9-11. In another exemplary embodiment, working channel 112 extends through body 114, as shown in FIGS. 12-14. In a further exemplary embodiment, working channel 112 extends through body 114 of adaptor 110 over a short distance, and working member 120 extends across the length of working channel 112, as shown in FIG. 18.

As shown in FIGS. 13 and 14, working member 120 may include a wedge 120a and a guide 120b. Wedge 120a may be a thin plate, such as a fin-shaped plate, that stems from the inner wall of working channel 112. Wedge 120a may extend up to the longitudinal axis of working channel, where it is connected with guide 120b. Guide 120b may have a tapered elongated shape that aligns with the longitudinal axis of working channel 112. When elongated device 300 is inserted though working channel 112, the distal end of elongated device 300 passes by working member 120. Wedge 120a of working member 120 opens up or widens a portion of slit 312 at the distal end of device 300, thereby allowing guidewire 200 to merge into slit 312. Wedge 120a also maintains the opening of slit 312 as device 300 passes by working member 120, thereby allowing for continuous merging of guidewire 200 into slit 312. Guide 120b may enter device 300, such as channel 310 of device 300, to maintain the direction of insertion of device 300 during its merge with guidewire 200. After the portion of slit 312 passes through working member 120, it returns to its natural width out of its own elasticity. Guidewire 200 may further merge into channel 310 of elongated device 300.

Adapter 110 may further include a side groove 115. In some embodiments, side groove 115 may extend across a ramp extending across body 114. When adapter 110 is engaged with main block 150, side groove 115 complement main groove 156 of main block 150 to provide a path for leading guidewire 200 towards main channel 154. In some embodiments, as shown in FIGS. 9-11, side groove 115 may extend up to a distal point 124 of working member 120 such that guidewire 200 is led towards longitudinal axis 124. This allows guidewire 200 to be aligned with elongated device 300 when elongated device 300 passes through working channel 112 along longitudinal axis 124, thereby naturally merging into elongated device 300 as elongated device 300 passes by working member 120 at distal point 124.

Figure 16A:
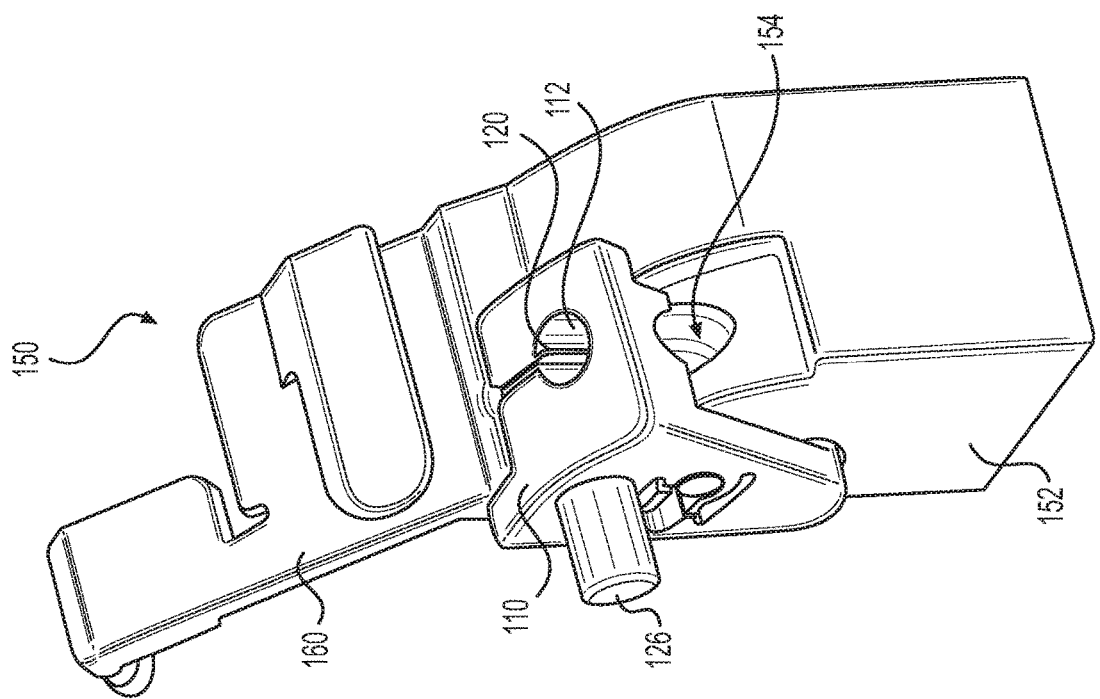
FIG. 16A is a partial perspective view of another exemplary adaptor engaged with the exemplary main block of FIG. 15 in an introduction-device mode, according to embodiments of the present disclosure.
Figure 16B:
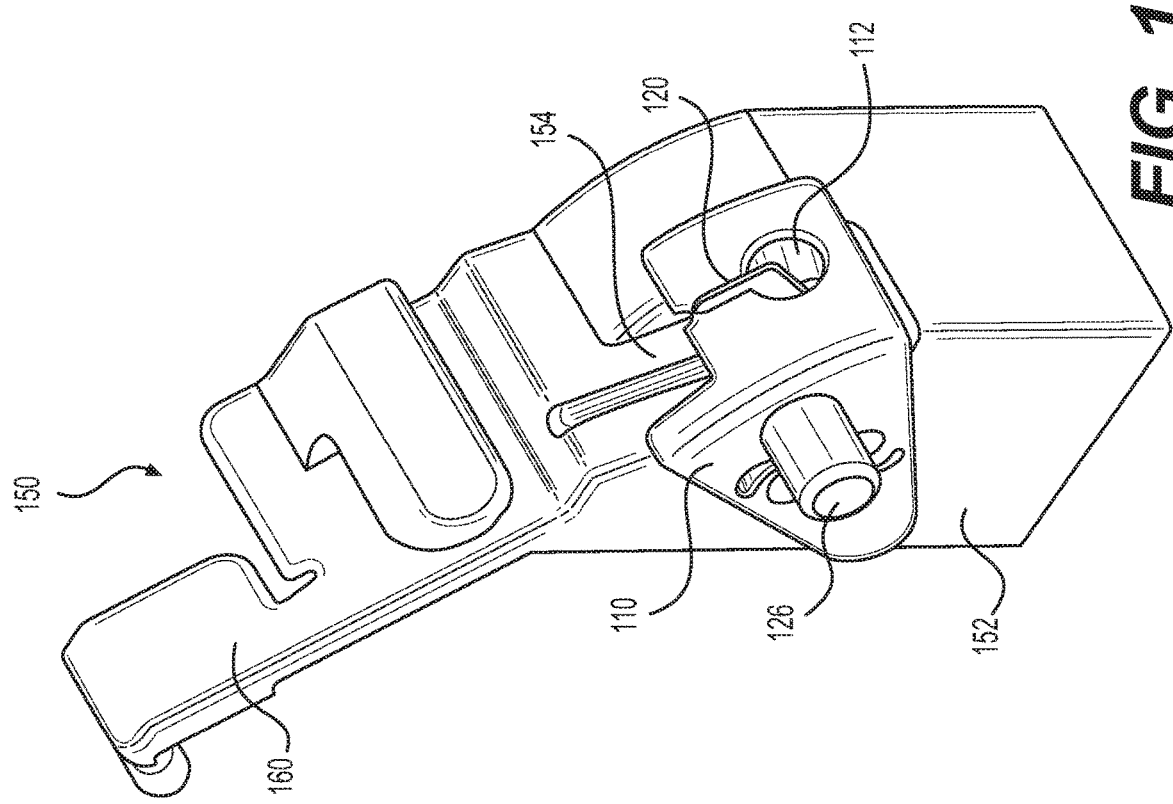
FIG. 16B is a partial perspective view of another exemplary adaptor engaged with the exemplary main block of FIG. 15 in a second-device mode, according to embodiments of the present disclosure.
Figure 17:
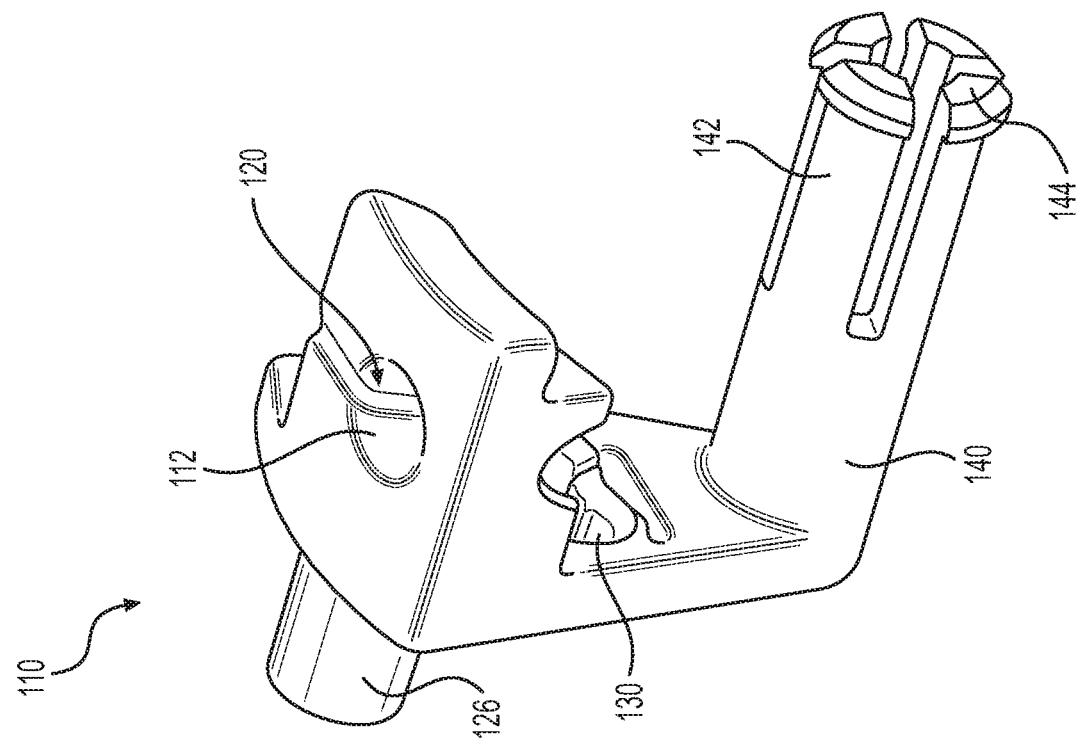
FIG. 17 is a perspective view of the exemplary adaptor of FIG. 16, according to embodiments of the present disclosure.

In some embodiments, main block 150 and adaptor 110 include suitable complementary fitting structures that allow adaptor 110 to be fixedly engaged with main block 150. FIG. 15 shows another exemplary embodiment of main block 150. FIGS. 16A and 16B show another exemplary embodiment of adaptor 110 fixedly engaged with the exemplary main block 150 of FIG. 15. FIG. 17 is a perspective view and FIG. 18 is a cross-sectional view of the exemplary embodiment of adaptor of FIGS. 16A and 16B.

As shown in FIGS. 15-16B, main block 150 may include a protrusion 157 and a conduit 159 configured to engage with a hole 130 and a fitting protrusion 140 of adaptor 110 respectively. Fitting protrusion 140 may include, for example, one or more prongs 142. When fitting protrusion 140 is inserted into conduit 159, for example, prongs 142 may deflect slighted inward so as to form a friction fit with conduit 159. The end of prongs 142 may have one or more stops 144 to engage with an opening of conduit 159 such that adaptor 110 is fixedly engaged with main block 150. As described herein, any suitable mechanical structures or connecting mechanisms may be used to securely engage adaptor 110 with main block 150.

Exemplary embodiments of adaptor 110 that can be fixedly engaged with main block 150 may have two working modes, an introduction-device mode, as shown in FIG. 16A, and a second-device mode, as shown in FIG. 16B. Adaptor 110 may be switched between these two modes as needed by a physician during an endoscopic procedure, such as by turning a control 126.

For example, when adaptor 110 is positioned in the introduction-device mode, working channel 112 of adaptor 110 is moved away the opening of main channel 154 such that a first elongated device 300 containing guidewire 200 (an introduction device) can be introduced directly into endoscope 400 through main channel 154 to approximate a desired treatment site. A diagnostic operation may be performed to determine the desired treatment site and guidewire 200 may be fixed in position by locking device 160 to maintain access to the desired treatment site.

To exchange the first elongated device 300 with a second elongated device 300, the first elongated device 300 may then be removed off guidewire 200 by being continuously split or torn away from guidewire 200 through slit 312 while guidewire 200 remain fixed by locking device 160. After the removal of the first elongated device 300, adaptor 110 is positioned in the second-device mode such that working channel 112 of adaptor 110 is aligned with main channel 154. The second elongated device 300 can then be merged with guidewire 200 as it is inserted into working channel 112 and then into endoscope 400 to reach the desired treatment site as further described below with reference to FIGS. 19A-20C.

Figure 19C:
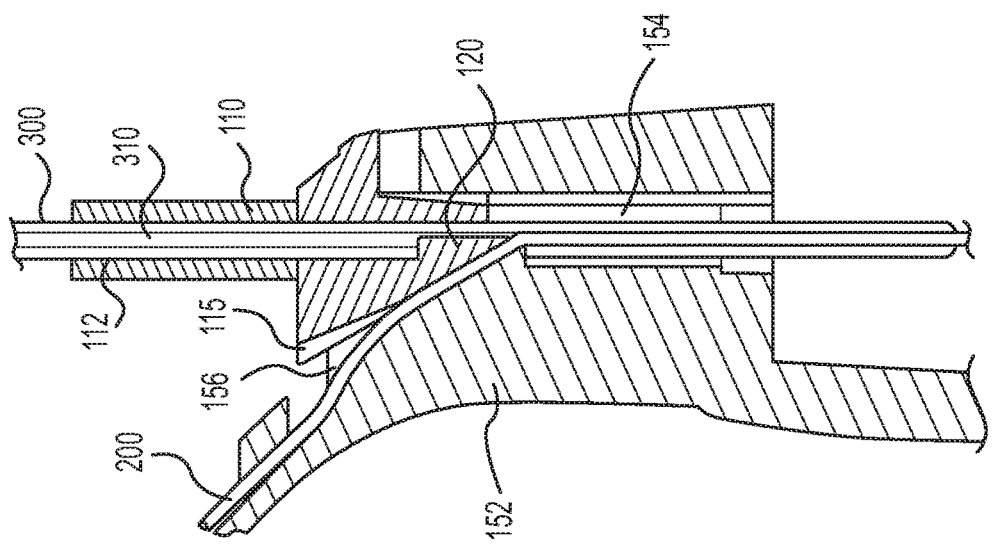
FIG. 19C is a perpendicular cross-sectional view of the exemplary system of FIG. 1, receiving the elongated device of FIG. 7, according to embodiments of the present disclosure.
Figure 19B:
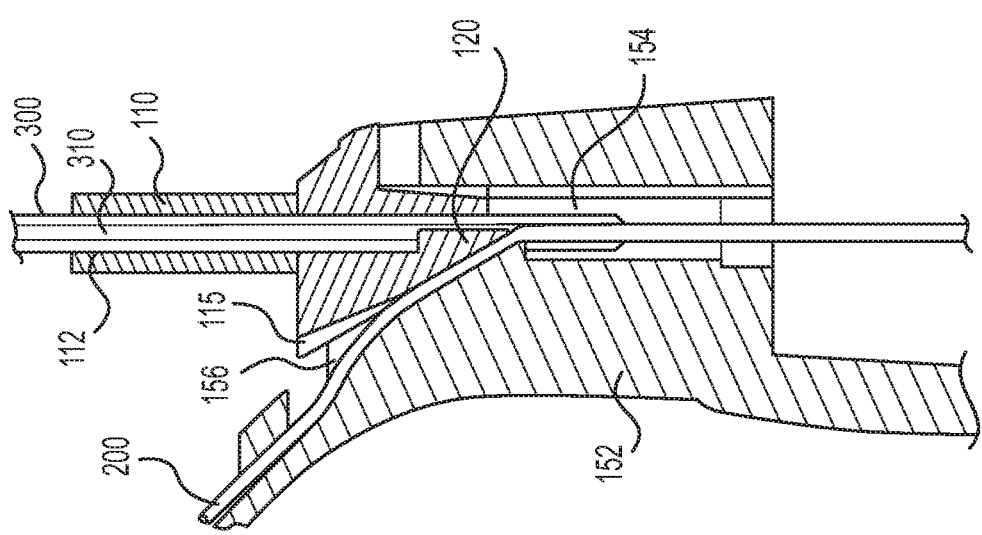
FIG. 19B is a perpendicular cross-sectional view of the exemplary system of FIG. 1, receiving the elongated device of FIG. 7, according to embodiments of the present disclosure.
Figure 19A:
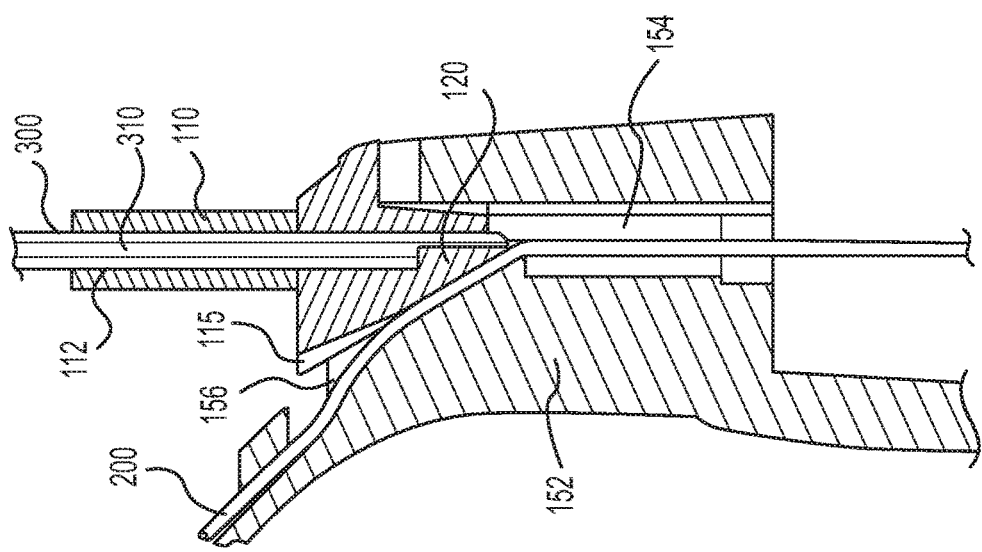
FIG. 19A is a perpendicular cross-sectional view of the exemplary system of FIG. 1, receiving the elongated device of FIG. 7, according to embodiments of the present disclosure.

FIGS. 19A-19C are perpendicular cross-sectional views of system 100 receiving elongated device 300 at different time points. As described above, before introducing elongated device 300 over guidewire 200, guidewire 200 can be held by locking device 160 in a predetermined position to maintain access to a desired treatment site. As shown in FIGS. 19A-19C, after passing through the locking features of locking device 160, guidewire 200 is received in a path formed by main groove 156 and side groove 115 and led towards distal end 124 of working member 120.

As shown in FIG. 19A, to introduce elongated device 300 over guidewire 200, a physician or an assistant may insert elongated device 300 into working channel 112 of adapter 110. In some embodiments, to facilitate the alignment of elongated device 300 with working member 120 and/or guidewire 200, the inner diameter of working channel 112 may be selected to substantially match an outer diameter of elongated device 300. As elongated device 300 passes through working channel 112, the distal end of elongated device 300 meets and passes by working member 120, which then wedges open a portion of slit 312 of elongated device 300. As shown in FIG. 19B, this in turn allows a portion of guidewire 200 at distal end 124 of working member 120 to merge into a corresponding portion of elongated device 300, e.g., a portion of channel 310, through the opened portion of slit 312. After guidewire 200 merges into the distal end of elongated device 300, as shown in FIG. 19C, guidewire 200 can continuously merge into elongated device 300 as elongated device 300 passes though working channel 112 until the distal end of elongated device 300 approximates or reaches the desired treatment site.

As described above, guidewire 200 is held in place by locking device 160 throughout the merging of guidewire 200 into elongated device 300. This advantageously reduces the risk of losing the access to the desired treatment site in the body of a patient and increases the effectiveness of the introduction of elongated device 300 over guidewire 200 in a minimum amount of time.

FIGS. 20A-20C are parallel cross-sectional views illustrating the merging of guidewire 312 into elongated device 300. As shown in FIG. 20A, the diameter of guidewire 312 is substantially greater than a natural width of slit 312. As described above in reference to FIGS. 19A-19C, before introducing elongated device 300, guidewire 200 has been aligned with distal point 124 of working member 120. When the distal end of elongated device 300 passes by working member 120, working member 120 then wedges open slit 312. Therefore, as shown in FIG. 20B, the opening of slit 312 provides a passage for guidewire 200 to merge into channel 310 of elongated device 300. After elongated device 300 passes by working member 120, as shown in FIG. 3C, slit 312 is no longer wedged opened and returns to its natural width, thereby at least partially enclosing guidewire 200 in channel 310 of elongated device 300. This advantageously allows guidewire 200 to be retained in channel 310 to effectively guide elongated device 300 to a desired treatment site before and during a medical operation.

As describe above, guidewire 200 may start merging into elongated device 300 from the distal end of elongated device 300 continuously up until the distal end of elongated device 300 approximate or reaches the desired treatment site. Advantageously, throughout the introduction of elongated device 300 over guidewire 200, guidewire 200 remains locked by locking device 160 to maintain access to the desired treatment site, thereby eliminating the need to manually holding guidewire 200 and reducing the risk of displacement of guidewire 200.

As described herein, elongated device 300 with slit 312 may be made of any suitable compliant polymeric material with adequate stiffness such that it can be wedged open and can close on its own. Such polymeric material may be selected from PTFE, Pebax, Nylon, Polyethylene, etc.

To retrieve elongated device 300 introduced over guidewire 200, a physician or an assistant may remove adapter 110 from main block 150 and pull elongated device 300 out of the lumen of endoscope 400 and main channel 154. Guidewire 200 can remain locked by locking device 160 so that another elongated device 300 may be introduced to the treatment site. During the retrieval of elongated device 300, to remove elongated device 300 off guidewire 200, the physician or assistant may separate elongated device 300 from guidewire 200 by continuously splitting or tearing elongated device 300 from guidewire 200 through slit 312.

System 100 described herein may be utilized in a variety of systems and methods for performing device exchange during endoscopic procedures. An exemplary method 500 may use system 100 or one or more features of the embodiments of system 100 described above in reference to FIGS. 1-20C. Exemplary embodiments of method 500 are described below with reference to FIGS. 21A and 21B.

As described herein, some or all steps of method 500 may be performed by system 100 or one or more components of system 100. The sequence of the steps of method 500 may change, and may be performed in various exemplary embodiments. Additional steps may be added to method 500. Some steps may be omitted or repeated, and/or may be performed simultaneously.

Figure 21A:
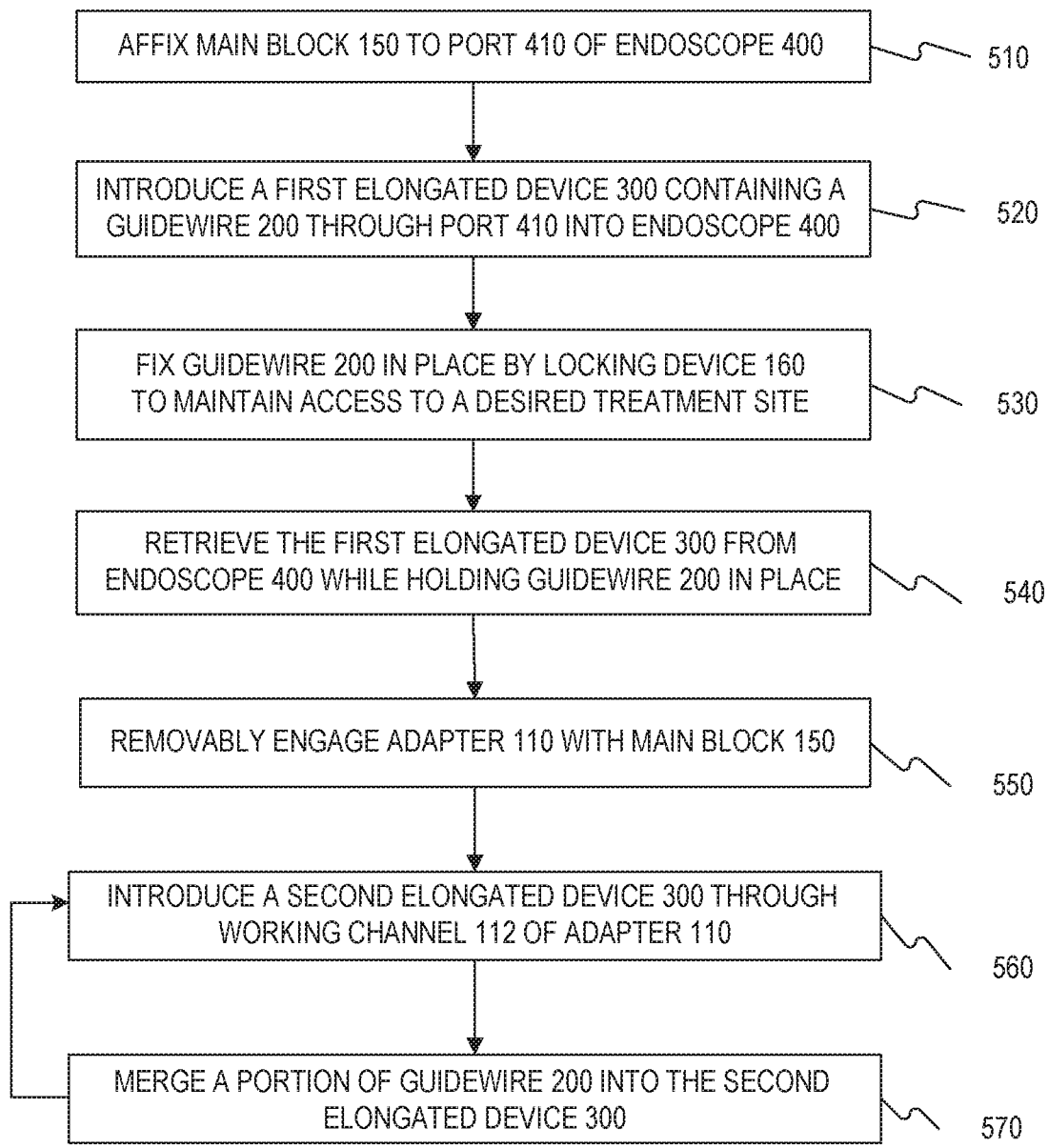
FIG. 21A is a flowchart of an exemplary method for device exchange, according to embodiments of the present disclosure.

As described above, in some embodiments, adaptor 110 can be removably engaged with main block 150. In such instances, method 500 may include steps 510-570 as shown in FIG. 21A. Step 510 may include affixing main block 150 of system 100 to port 410 of endoscope 400. For example, fastener 190 may be used to securely attach main block 150 on top of port 410 such that main channel 154 aligns with the inner lumen of port 410.

Step 520 may include introducing a first elongated device 300 containing a guidewire 200 through port 410 into endoscope 400 to approximate a desired treatment site. Step 510 may further include performing a diagnostic operation to determine the desired treatment site.

Step 530 may include fixing guidewire 200 in place to maintain access to the desired treatment site. Step 530 may further include frictionally fixing guidewire 200 in place by a plurality of zigzag locking features of locking device 160 of main block 150.

Step 540 may include retrieving the first elongated device 300 from endoscope 400 while fixing guidewire 200 in place by locking device 160. Step 540 may further include continuously splitting the first elongated device 300 from a proximal end of guidewire 200 through slit 312 until the first elongated device 300 is completely removed off guidewire 200.

Step 550 may include removably engaging adapter 110 with main block 150. Step 550 may further include removably engaging adapter 110 with an opening of main channel 154 of main block 150. For example, adaptor 110 may engage with main channel 154 via frictional fit, threaded fit, or other suitable fitting mechanism. Additionally or alternatively, step 550 may include engaging adaptor 110 with main block 150 using a detent, a fastener, and/or other suitable structures to securely hold adapter 110 thereon.

Step 560 may include introducing a second elongated device 300 through working channel 112 of adapter 110. Step 560 may further include passing the distal end of the second elongated device 300 by working member 120 of adapter 110 and wedging open a portion of slit 312 of the second elongated device 300 by working member 120.

Step 570 may include merging a portion of guidewire 200 into the second elongated device 300 through the opened portion of slit 312. Step 570 may further include, after merging the portion of guidewire 200 into the second elongated device 300, receiving the portion of guidewire 200 in partially enclosed channel 310 of second elongated device 300. Step 570 may further include closing or narrowing the opened portion of slit 312 to retain the portion of guidewire 200 in channel 310 after the corresponding portion of the second elongated device 300 passes by working member 120. Steps 560 and 570 may be performed continuously until the distal end of the second elongated device 300 reaches the desired treatment site.

Figure 21B:
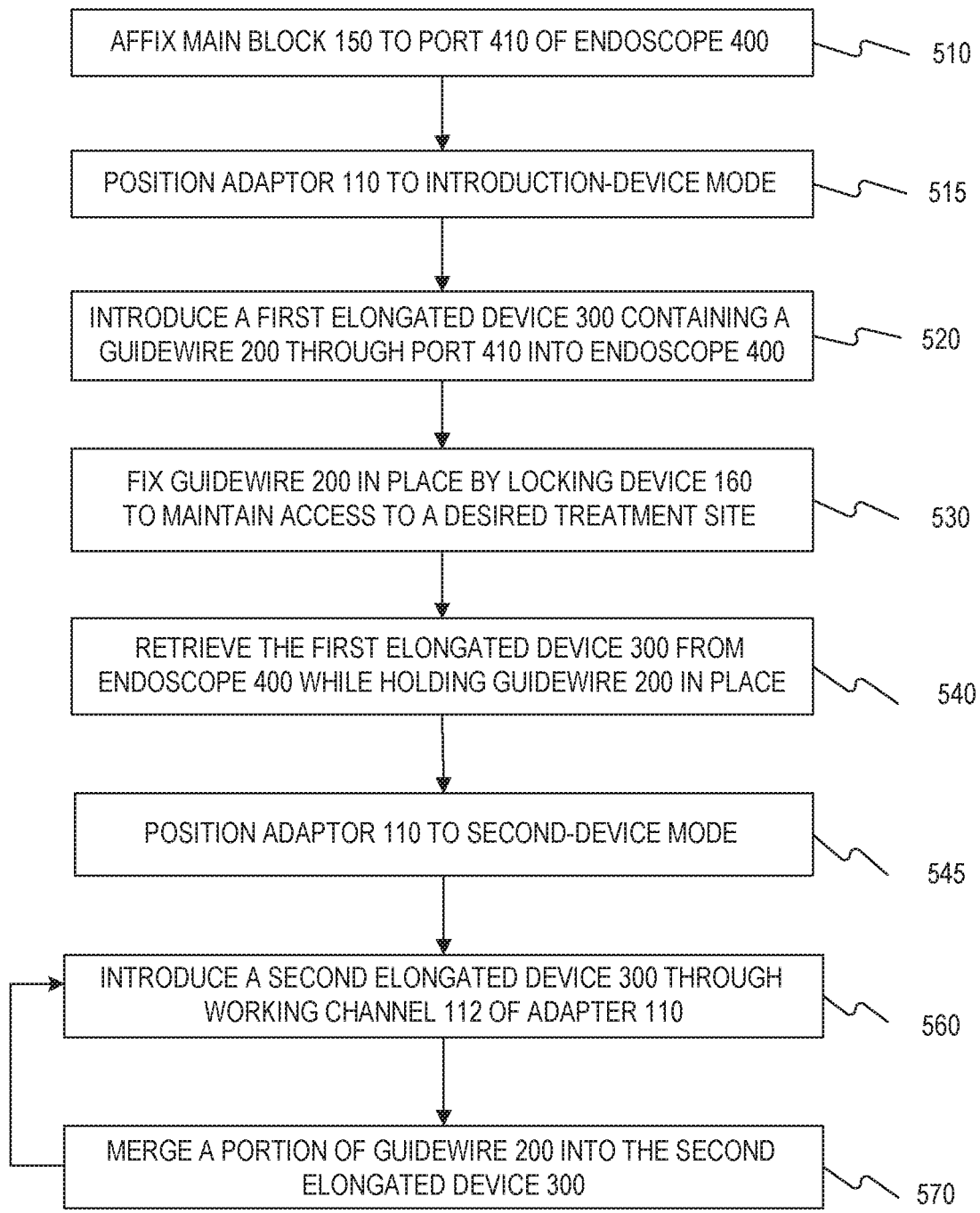
FIG. 21B is a flowchart of another exemplary method for device exchange, according to embodiments of the present disclosure.

In other embodiments, adaptor 110 can be fixedly engaged with main block 150, as described above with reference to FIGS. 15-18. In such instances, method 500 may further include steps 515 and 545 as shown in FIG. 21B. Step 515 may include positioning adaptor 110 in the introduction-device mode such that a first elongated device 300 containing guidewire 200 can be introduced into endoscope 400 to approximate a desired treatment site. Step 515 may further include performing a diagnostic operation to determine the desired treatment site. Step 545 may include positioning adaptor 110 in the second-device mode. In such instances, rather than performing step 550 to engage adaptor 110 with main block 150, step 545 adjusts the position of adaptor 110 that has been fixedly engaged with main block 150, allowing for the alignment of working channel 112 of adaptor 110 with main channel 154.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A system for device exchange in an endoscopic procedure, the system comprising:
    an elongated device having a slit extending from a distal tip to a proximal end of the elongated device;
    a main block configured to be affixed to a port of an endoscope, the main block comprising
        a main channel for receiving at least one guidewire and the elongated device, and
        a main groove that provides a path leading the least one guidewire towards a longitudinal axis of the main channel; and
    an adapter engaged with the main block and configured to merge the guidewire into the elongated device, the adapter comprising:

a working channel for receiving the elongated device; and a working member extending from an inner wall of the working channel;

wherein when the elongated device passes through the working channel, the working member wedges open a portion of the slit of the elongated device such that a portion of the guidewire merges into the elongated device through the opened portion of the slit.

2. The system of claim 1, wherein the adapter is capable of merging the guidewire into the elongated device continuously from a distal end of the elongated device until it reaches a desired treatment site.

3. The system of claim 1, wherein the working member aligns with a longitudinal axis of the working channel and the longitudinal axis of the main channel when the adapter is engaged with the main block.

4. The system of claim 3, wherein the adapter further comprises a body to be fitted into an opening of the main channel.

5. The system of claim 4, wherein the body further comprises a side groove at least partially complements the main groove and extends to a distal end of the working member.

6. The system of claim 1, wherein a natural width of the slit is substantially smaller than the diameter of the guidewire.

7. The system of claim 6, wherein after merging into the elongated device, the portion of the guidewire is received by a partially enclosed channel in the elongated device connected to the slit.

8. The system of claim 7, wherein the opened portion of the slit returns to the natural width after passing by the working member such that the portion of the guidewire is retained in the partially enclosed channel of the elongated device.

9. The system of claim 1, wherein the working channel of the adapter has a predetermined inner diameter that substantially matches an outer diameter of the elongated device.

10. The system of claim 1, wherein main block further comprises a locking device for fixing the guidewire in a predetermined position.

11. The system of claim 10, wherein the locking device further comprises zigzag locking features that frictionally maintain the guidewire in the predetermined position.

12. The system of claim 10, wherein the main block further comprises at least one secondary locking device for fixing at least one additional guidewire in a predetermined position.

13. The system of claim 1, wherein the main block further comprises a fastener that affixes the main block to the port of the endoscope.

14. The system of claim 1, wherein the main block and the adapter further comprise complementary fitting structures configured to engage the adapter with the main block.

15. The system of claim 1, wherein the adaptor is fixedly or removably engaged with the main block.

16. A method for device exchange in an endoscopic procedure, the method comprising:

providing an elongated device having a slit extending from a distal tip to a proximal end of the elongated device;

providing an apparatus for device exchange, the apparatus comprising a main block and an adapter, the main block comprising a main channel for receiving a guidewire and the elongated device and a main groove that provides a path leading the guidewire towards a longitudinal axis of the main channel, the main block being configured to attach to a port of an endoscope; and the adapter comprising a working channel for receiving the elongated device and a working member extending from an inner wall of the working channel, the adapter being configured to engage with the main block, receiving the elongated device through the working channel of the adapter such that the elongated device passes by the working member;

wedging open a portion of a slit of the elongated device by the working member; and merging a portion of the guidewire into the elongated device through the opened portion of the slit.

17. The method of claim 16, further comprising merging the guidewire into the elongated device continuously from a distal end of the elongated device until it reaches a desired treatment site.

18. The method of claim 16, further comprising, before receiving the elongated device, fixing the guidewire in a predetermined position by a locking device of the main block; and engaging the adapter with an opening of the main channel.

19. The method of claim 18, further comprising, before engaging the adapter with the opening of the main channel, retrieving a prior elongated device previously introduced over the guidewire from the main channel by continuously splitting prior elongated device from a proximal end of the guidewire through a slit extending over the length of the prior elongated device.

20. The method of claim 16, wherein a natural width of the slit is substantially smaller than the diameter of the guidewire.

21. The method of claim 20, further comprising, after merging the portion of the guidewire into the elongated device, receiving the portion of the guidewire in a partially enclosed channel in the elongated device connected to the slit.

22. The method of claim 21, further comprising retaining the portion of the guidewire in the partially enclosed channel of the elongated device.

23. An apparatus for device exchange in an endoscopic procedure, the apparatus comprising:

a main block configured to be affixed to a port of an endoscope, the main block comprising a main channel for receiving a guidewire and an elongated device having a slit extending over its length, and a main groove that provides a path leading the guidewire towards a longitudinal axis of the main channel; and an adapter engaged with the main block and configured to merge the guidewire into the elongated device, the adapter comprising:

a working channel for receiving the elongated device; and a working member extending from an inner wall of the working channel;

wherein when the elongated device passes through the working channel, the working member wedges open a portion of the slit of the elongated device such that a portion of the guidewire merges into the elongated device through the opened portion of the slit.

24. An adapter for merging a guidewire into an elongated device, the adapter comprising:

a working channel having an inner wall, the working channel for receiving an elongated device having a slit extending from a distal tip to a proximal end of the elongated device;

a working member extending from an inner wall of the working channel; and a side groove extending to a distal end of the working member;

wherein when the elongated device passes through the working channel, the working member wedges open a portion of the slit of the elongated device such that a portion of the guidewire merges into the guidewire channel through the opened portion of the slit.

25. An adapter for merging a guidewire into an elongated device, comprising:

means for receiving an elongated device, wherein an elongated device has at least one longitudinal axis, a guidewire lumen, and a slit extending from a distal tip to a proximal end of the elongated device;

means for receiving and directing a guidewire towards one elongated device longitudinal axis; and means for opening a portion of an elongated device slit such that a portion of a guidewire received in said receiving and directing means merges into an elongated device slit opened portion.

* * * * *